(12) United States Patent
Lou

(10) Patent No.: US 10,441,099 B2
(45) Date of Patent: Oct. 15, 2019

(54) MAGNETIC MOXIBUSTION PILLOW

(71) Applicant: Zhongping Lou, Hangzhou (CN)

(72) Inventor: Zhongping Lou, Hangzhou (CN)

( * ) Notice: Subject to any disclaimer, the term of this patent is extended or adjusted under 35 U.S.C. 154(b) by 494 days.

(21) Appl. No.: 15/275,380

(22) Filed: Sep. 24, 2016

(65) Prior Publication Data
US 2017/0181554 A1    Jun. 29, 2017

(30) Foreign Application Priority Data

Dec. 28, 2015  (CN) .................. 2015 2 1113288 U

(51) Int. Cl.
*A47G 9/00*  (2006.01)
*A61H 99/00*  (2006.01)
*A47G 9/10*  (2006.01)

(52) U.S. Cl.
CPC ............... *A47G 9/007* (2013.01); *A47G 9/10* (2013.01); *A47G 9/1081* (2013.01); *A61H 99/00* (2013.01); *A47G 2009/004* (2013.01); *A61H 2201/10* (2013.01)

(58) Field of Classification Search
CPC ........... A61N 2/002; A61F 5/055; A61F 7/02; A61F 2007/0011; A61F 2007/0206
See application file for complete search history.

(56) References Cited

U.S. PATENT DOCUMENTS

| | | | |
|---|---|---|---|
| 5,344,384 A * | 9/1994 | Ostrow | A61N 1/325 600/13 |
| 5,950,239 A * | 9/1999 | Lopez | A41B 9/00 2/113 |
| 2009/0050657 A1* | 2/2009 | Woolery | A45F 3/14 224/183 |

* cited by examiner

*Primary Examiner* — Christine H Matthews
*Assistant Examiner* — Joshua Daryl D Lannu
(74) *Attorney, Agent, or Firm* — Leon E. Jew; Dahyee Law Group

(57) ABSTRACT

The present invention teaches a negative magnetic field magnetic moxibustion pillow which includes a pillow noumenon and multiple magnets set inside the described pillow noumenon. The described multiple magnets are set on the substrate based on a preset spacing; one end of the described magnets is a positive pole, and the other end is a negative pole. Moreover, the negative pole of the magnets all face the top surface of the pillow noumenon while the negative magnetic field magnetic moxibustion pillow of this present invention can produce a relatively strong magnetic field for the user.

5 Claims, 4 Drawing Sheets

MAGNETIC MOXIBUSTION PILLOW

REFERENCE TO RELATED APPLICATIONS

The present invention claims the priority date of the Chinese Patent Application No. 201521113288 which was filed on Dec. 28, 2015.

FIELD OF THE INVENTION

The present invention generally relates to the field of magnetic therapy. More particularly, the invention relates to a negative magnetic field magnetic moxibustion pillow which enhances the efficacy of magnetic therapy.

BACKGROUND OF THE INVENTION

In recent years, magnetotherapy has been developed rapidly due to its adaptability to a wide range of symptoms, significant health effect, non-invasiveness, no pain, little side effects, safety, reliability, ease to learn, cheapness, and other advantages. It has now been a new type of treatment method that is widely promoted. Magnetotherapy is so-called therapy by creating a magnetic field, which is a common name for treatment of diseases by applying a magnetic force. Normally, the site that is going to be treated is placed in a dynamic magnetic field in order to achieve the goal of promoting blood circulation, removing blood stasis, reducing swelling, relieving pain, diminishing inflammation, analgesia, by impacting human tissues based on the magnetism produced by magnetic poles.

For current magnetotherapy pillow, the magnetic material is usually set inside the pillow. During application, the magnetic lines produced by magnetic material will act on the user and conduct magnetotherapy. However, in current magnetotherapy products, the magnetic material is normally randomly distributed, in which case energy of the magnetic field produced by each magnetic material may cancel each other, causing poor magnetotherapy efficacy. What is desirable is a negative magnetic field magnetic moxibustion device which uses magnets with a negative and positive poles. The assembly method then will require the negative pole of the magnets to face one direction and produce a relatively strong magnetic field which further solves the current unreasonable disposal of magnetic field energy in current existing devices.

SUMMARY OF THE INVENTION

Accordingly, the present invention is a negative magnetic field magnetic moxibustion pillow which includes a pillow noumenon and multiple magnets set inside the described pillow noumenon. The described multiple magnets are set on the substrate based on a preset spacing; one end of the described magnets is a positive pole, and the other end is a negative pole. Moreover, the negative pole of the magnets all face the top surface of the pillow noumenon while the negative magnetic field magnetic moxibustion pillow of this present invention can produce a relatively strong magnetic field on the whole upper body, and solves the technique problem in current magnetic moxibustion pillow of poor magnetotherapy efficacy due to unreasonable disposal of magnetic material.

In the most preferred embodiment of the present invention, the negative field magnetic moxibustion pillow solves the technique problem in current magnetotherapy products of poor magnetotherapy efficacy due to unreasonable disposal of magnetic material. This invention provides a negative magnetic field magnetic moxibustion pillow. The pillow noumenon includes a top surface to support the human body with a concave surface to support the head and a convex surface to support the cervical vertebrae. There is a transitional connection between the concave surface and convex surface which includes multiple magnets set inside the pillow noumenon. The multiple magnets are set on the substrate based on a preset spacing. One end of the described magnets is a positive pole, and the other end is a negative pole. The negative pole of the multiple magnets all faces the top surface of the pillow noumenon while the substrate itself, includes a primary substrate and a secondary substrate. The primary magnets among the described multiple magnets are set on the primary substrate based on the preset primary spacing along the longitudinal direction of the pillow noumenon. The secondary magnets among the described multiple magnets are set on the secondary substrate based on the preset secondary spacing, and the elongation direction of the described magnetic stripes is the same with the longitudinal direction of the pillow noumenon. The magnetic stripes are then set based on the preset third spacing. In addition, the secondary substrate is set at the center of the pillow noumenon while the preset primary spacing and secondary spacing are equal lengths. Furthermore, the multiple magnets are set on the substrate through the multiple grooves on the substrate, and the magnets are protruded from the grooves while each groove corresponds to one magnet.

Yet in another embodiment of the present invention, instead of using grooves to place each magnet, the magnets can be set on the substrate by sewing or adhesion.

DETAILED DESCRIPTION OF THE INVENTION

Figure 1:
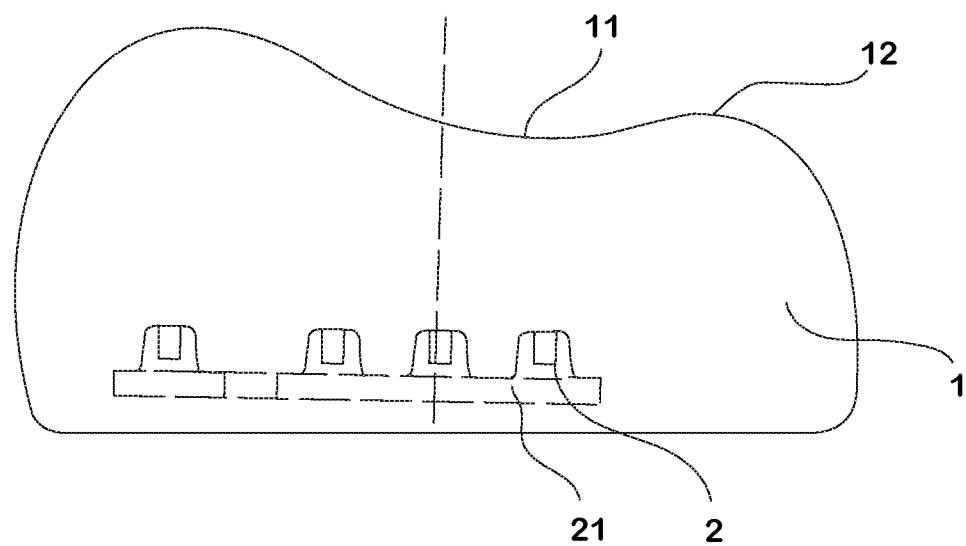
FIG. 1 is an illustration of the overall structure of the negative magnetic field magnetic moxibustion pillow of the present invention shown from the side view.

While the present invention may be embodied in many different forms, designs or configurations, for the purpose of promoting an understanding of the principles of the invention, reference will be made to the embodiments illustrated in the drawings and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

Figure 2:
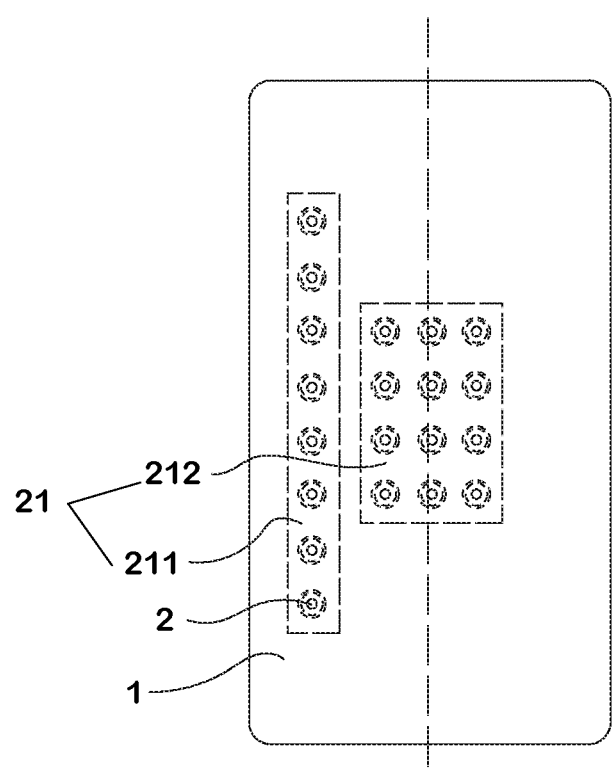
FIG. 2 is an illustration of the top view of the negative magnetic field magnetic moxibustion pillow of the present invention.

FIG. 1 is an illustration of the preferred embodiment of the negative field magnetic moxibustion pillow for the present invention shown from the side view. FIG. 2 is a top view illustration of one embodiment of the negative field magnetic moxibustion pillow for the present invention. Both FIG. 1 and FIG. 2 illustrate the pillow noumenon 1, including the top surface to support the human body with a concave surface 11 to support the head. A convex surface 12 to support the cervical vertebrae is also shown. A transitional connection between the concave surface 11 and convex surface 12 includes multiple magnets 2 set inside the pillow noumenon 1, and the multiple magnets 2 are set on the substrate 21 based on the preset spacing. On one end of the magnets 2 is a positive pole, and the other is a negative pole. Negative poles of the magnets 2 all face the top surface of the pillow noumenon. Since FIG. 1 is a side view illustration along the longitudinal direction of the pillow noumenon, multiple magnets 2 are set inside the pillow noumenon 1 and set on the substrate 21. One end of the magnets 2 faces the substrate 21, and the other end faces the top surface of the pillow noumenon. Moreover, in this embodiment, one end of the magnets 2 is a positive pole and the other is a negative pole. The positive poles of all the magnets 2 face the substrate 21, and all negative poles face the top surface of the pillow noumenon. As shown in FIG. 2, a quantity of 20 magnets 2 are set on the substrate 21, and negative poles of the quantity 20 magnets 1 all face upward. This way more negative poles will face the users when the users' head is on the pillow noumenon top surface. In this instance, the magnetic lines produced by negative poles can act on the users quickly. Furthermore, a negative magnetic field strength produced by negative poles is relatively large, which can enhance magnetotherapy efficacy and effectively activate body functions.

The multiple magnets 2 are magnetically permeable material while the substrate is not magnetically permeable in order to prevent intervention of substrate on multiple magnetic stripes. The substrate 21 can also be a flexible material for ease of manufacturability as well. Therefore, by setting multiple magnets inside the pillow noumenon with positive poles facing the substrate and negative poles facing the top surface of the noumenon, more negative poles will be closer to the users during the application process, in which case the magnetic lines produced by negative poles can quickly act on the users. Thus, users are inside the negative magnetic field formed by magnetic lines from negative poles. Then the magnetic field strength of the negative magnetic field can be maintained at a constant, and it can effectively activate the body functions and enhance magnetotherapy efficacy.

Furthermore, the described substrate 21 includes the primary substrate 211 and the secondary substrate 212. The primary magnets in the multiple magnets are fixed on the primary substrate 211 and arranged along the longitudinal direction of the pillow noumenon based on the preset primary spacing. The secondary magnets in the described multiple magnets are set on the described secondary substrate 212 based on the secondary spacing in order to form multiple magnetic stripes. The elongation direction of the described magnetic stripes is the same with the longitudinal direction of the pillow noumenon while the described magnetic stripes are set based on the third preset spacing.

In particular, as shown in FIG. 2 magnets can be divided into two parts. One part is the primary magnets, which are set on the primary substrate 211, and they are arranged based on the preset primary spacing along the longitudinal direction of the pillow noumenon. The other part is the secondary magnets, which are set on the secondary substrate 212, and they are arranged based on the preset secondary spacing along the longitudinal direction of the pillow noumenon to form multiple magnetic stripes. The described magnetic stripes are set based on the preset third spacing, and the distance between each magnetic stripe can be equal or unequal. As shown in FIG. 2, the described secondary substrate 212 is set at the center of the pillow noumenon, and the preset primary spacing and secondary spacing is the same.

When multiple magnets 2 are set on the substrate 21, they are arranged along the longitudinal direction with equal spacing. The preset primary and secondary spacing between magnets 2 can be 20-40 mm. In this case, it is guaranteed that the multiple magnets 2 can form a relatively large and uniform magnetic field strength. Thus, when the magnetic field acts on human beings or animals, it has a stronger penetration force. The magnetic lines can penetrate into the skin, which enhances its function on human or animal bodies, and can improve their microcirculation. Furthermore, the multiple magnets 2 are set on the substrate 21, and multiple grooves can be set on the substrate 21. The multiple magnets 2 can be set inside the grooves, and in this case magnets 2 are fixed and distributed on the substrate 21. Every groove then corresponds to one magnet 2, and as shown in FIG. 2, the described magnets 2 are protruded out from the grooves.

Figure 3:
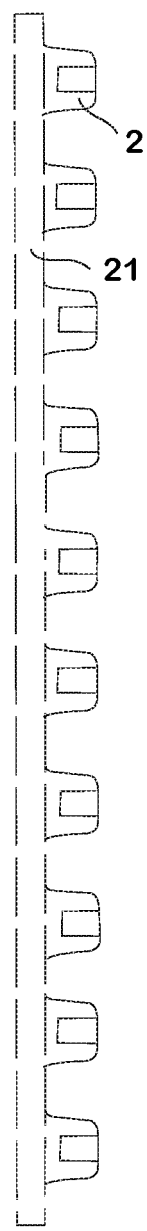
FIG. 3 is an illustration of the primary substrate for one embodiment of the negative magnetic field magnetic moxibustion pillow.
Figure 4:
FIG. 4 is an illustration of the top view of FIG. 3.

FIG. 3 shows an illustration of the side view of the primary substrate 21 of the present invention while FIG. 4 is a top view illustration of FIG. 3. As shown in FIG. 3, the thickness of the primary substrate 21 is 17 mm, and 30 mm with the magnets included. As shown in FIG. 4, the width of the primary substrate 21 is 50 mm, and the length is 400 mm.

Figure 5:
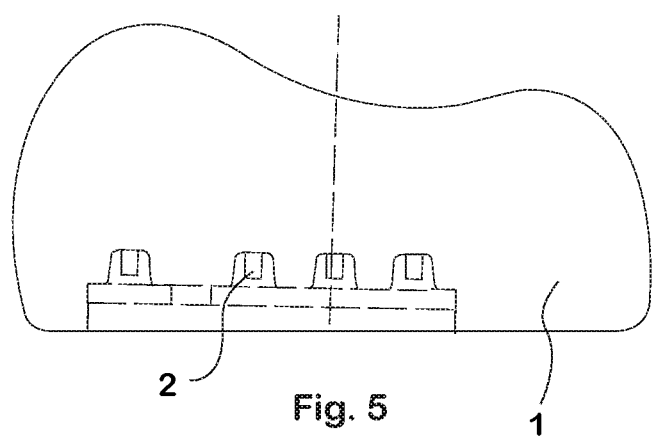
FIG. 5 is a side view illustration of the pillow noumenon for one embodiment of the negative magnetic field magnetic moxibustion pillow of the present invention.

FIG. 5 is a side view illustration of the pillow noumenon of the present invention. As shown in FIG. 5, the height of the substrate 21 inside the pillow noumenon is 10 mm, and the distance between the inner edge of the primary substrate 21 and central line of noumenon along the longitudinal direction is 102 mm.

Figure 6:
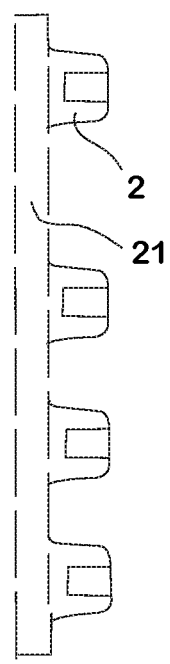
FIG. 6 is a side view illustration of the secondary substrate for one embodiment of the negative magnetic field magnetic moxibustion pillow of the present invention.
Figure 7:
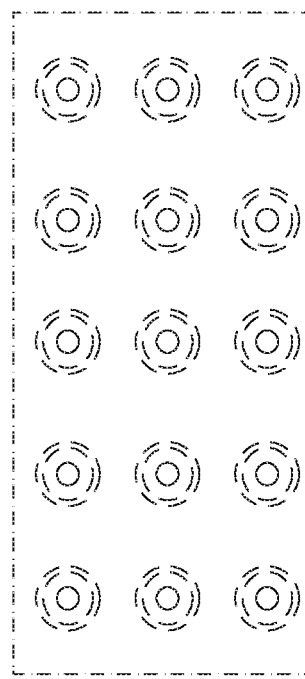
FIG. 7 is a top view illustration of FIG. 6.

FIG. 6 is a side view illustration of the primary substrate of the present invention while FIG. 7 is a top view illustration of FIG. 6. A shown in FIG. 6, the thickness of the secondary substrate is 17 mm, and 30 mm with the magnets included. As shown in FIG. 7, the width for the primary substrate is 150 mm and the length is 200 mm. In this example, when the thickness for substrate is relatively small or its material is soft, multiple magnets 2 can be fixed on substrate through adhesion or sewing. Furthermore, the magnetic field strength produced by the magnets 2 is larger than 1000 Gauss, in which case the field strength is larger than 1000 Gauss by using multiple magnets 2, resulting in a good magnetotherapy efficacy when it acts on human bodies.

Although one or more embodiments of the newly improved invention have been described in detail, one of ordinary skill in the art will appreciate the modifications to the material selection and utility functions of the moxibustion pillow along with the new newly improved assembly of positioning the negative pole of the magnets in a position facing the top surface of the pillow to avoid unreasonable disposal of magnetic material. Therefore, a desirable assembly and more effective footprint are created to enhance magnetic moxibustion therapy for humans. It is acknowledged that obvious modifications will ensue to a person skilled in the art. The claims which follow will set out the full scope of the claims.

The invention claimed is:

1. A negative magnetic field magnetic moxibustion pillow comprising:

a pillow having a top surface, a bottom surface, a concave surface, and a convex surface, wherein a transitional connection is between the concave surface and convex surface;

primary magnets and secondary magnets having a negative pole and positive pole; and a substrate wherein the primary and secondary magnets are set on the substrate based on a preset spacing inside the pillow;

wherein the negative pole of the primary and secondary magnets all face the top surface of the pillow;

wherein the substrate has a primary substrate and a secondary substrate;

wherein the primary magnets are fixed on the primary substrate and arranged along the longitudinal direction of the pillow based on a primary spacing;

wherein the secondary magnets are set on the secondary substrate based on a secondary spacing and forms magnetic stripes;

wherein an elongation direction of the magnetic stripes is the same longitudinal direction of the pillow; and wherein the magnetic stripes are set based on a third spacing.

2. The negative magnetic field magnetic moxibustion pillow of claim 1, wherein the secondary substrate is set along a central line which is along the pillow's longitudinal direction.

3. The negative magnetic field magnetic moxibustion pillow claim of 1, wherein the primary spacing is the same as the secondary spacing.

4. The negative magnetic field magnetic moxibustion pillow claim of 1, wherein the magnets are set on the substrate through multiple grooves on the substrate, wherein every groove corresponds to one of the magnets, and wherein the magnets are protruded from the grooves.

5. The negative magnetic field magnetic moxibustion pillow of claim 1, wherein the magnets are set on the substrate through sewing or adhesion.

* * * * *